(12) United States Patent
Marshall et al.

(10) Patent No.: US 8,491,841 B2
(45) Date of Patent: Jul. 23, 2013

(54) PRESSURIZED GAS PURGE SEAL FOR COMBUSTION FURNACE

(75) Inventors: Kim A. Marshall, St. Joseph, MI (US); Steven J. Rohaly, Benton Harbor, MI (US); Carl Warren, Stevensville, MI (US)

(73) Assignee: Leco Corporation, St. Joseph, MI (US)

( * ) Notice: Subject to any disclaimer, the term of this patent is extended or adjusted under 35 U.S.C. 154(b) by 220 days.

(21) Appl. No.: 12/853,638

(22) Filed: Aug. 10, 2010

(65) Prior Publication Data
US 2012/0039749 A1 Feb. 16, 2012

(51) Int. Cl.
*G01N 31/12* (2006.01)
*B01L 99/00* (2010.01)

(52) U.S. Cl.
USPC ............................................ 422/78; 422/568

(58) Field of Classification Search
USPC .......................................................... 422/78
See application file for complete search history.

(56) References Cited

U.S. PATENT DOCUMENTS

| | | | |
|---|---|---|---|
| 3,923,464 A * | 12/1975 | Sitek et al. | 422/78 |
| 5,064,617 A | 11/1991 | O'Brien et al. | |
| 5,314,662 A | 5/1994 | Hemzy et al. | |
| 5,395,586 A * | 3/1995 | Hemzy et al. | 422/63 |

* cited by examiner

*Primary Examiner* — Sam P Siefke
*Assistant Examiner* — Bryan Kilpatrick
(74) *Attorney, Agent, or Firm* — Price Heneveld LLP

(57) ABSTRACT

An analytical combustion furnace has an input port for receiving a holder for an analytical sample. A purge block is coupled to the input port of the combustion furnace and has an input end for receiving the holder and a gas inlet and a gas outlet. A door selectively closes the input end of the purge block, and a pressurized seal is coupled between the purge block and the door. A source of purging gas is coupled to the gas inlet of the purge block for pressurizing the seal. The gas outlet of the purge block communicates with the seal to allow purging gas to escape the area of the seal. In one embodiment, a pressurized seal surrounds a push rod, which seal is pressurized by a purging gas to continuously purge the entry of the push rod into the purge block, thereby eliminating atmospheric contamination.

22 Claims, 11 Drawing Sheets

PRESSURIZED GAS PURGE SEAL FOR COMBUSTION FURNACE

BACKGROUND OF THE INVENTION

The present invention relates to combustion furnaces and particularly to improved seals for sealing the entry to such furnaces.

Analyzers for elements, such as carbon, sulfur, and nitrogen, require the combustion of specimens, typically solids or liquids, in a holder, such as a crucible or combustion boat. In many instruments, the holder for the combustion sample is a ceramic holder. Horizontal furnaces, such as described in U.S. Pat. No. 5,064,617 issued Nov. 12, 1991, to O'Brien et al., the disclosure of which is incorporated herein by reference, utilize a ceramic combustion boat which is extended within an electrically heated furnace for combusting samples within a ceramic combustion chamber to temperatures of from about 1000° C. to about 1500° C. U.S. Pat. No. 5,314,662, issued May 24, 1994, to Heinz et al., discloses one system for automatically sequentially loading specimens into such a furnace and includes a mechanism for the admission and withdrawal of a combustion boat for an analysis. The disclosure of the U.S. Pat. No. 5,314,662 patent is also incorporated herein by reference.

With the increasing interest in the accurate determination of low concentration levels of elements, such as nitrogen, by various industries, the sealing of the furnace's entry way against atmospheric contaminants is becoming increasingly important. Although O-ring face-type seals have been employed in the past as has the use of purging gases in a purge block holding the combustion sample prior to entry into the furnace, such seals still can allow the admission of some atmospheric nitrogen, particularly where a push-rod is employed which extends through the purge block to position a sample holder, such as a combustion boat, into the combustion furnace itself. Also, the combustion furnace must be opened for the removal of a spent combustion boat and the admission of a new specimen in a new combustion boat. This process also allows the admission of atmospheric nitrogen and other atmospheric contaminants which must then be purged from the system.

Although existing furnace seals and purge blocks provide acceptable results, with the increasing industry demand for the measurement of low concentrations of analytes such as nitrogen, they are often limited by how the atmospheric nitrogen content impacts the blank measurement. As an example, if the blank nitrogen level was 50 ppm as when UHP oxygen (99.995%) is used as a carrier gas during an analysis, nitrogen levels in the surrounding atmosphere is more than 15,000 times the nitrogen level found in the blank. Thus, in order to achieve low level blanks, all atmospheric contamination must be avoided or eliminated. Thus, not only must the atmosphere be purged for the sample compartment but seals used to isolate the sample compartment from the surrounding environment must be highly effective. This is a major challenge where the seals must be cycled open during each sample to introduce new samples into the purge block sample-holding compartment.

In addition, sliding seals employed with push-pull rods for the introduction and withdrawal of samples from a furnace also present a challenge for maintaining effective isolation of the combustion chamber from the surrounding atmospheric environment. Small imperfections or scratches in the sliding rod can allow environmental contamination into the chamber and any other leaks likewise contaminate the specimen to be combusted and analyzed.

SUMMARY OF THE INVENTION

The system of the present invention solves these problems by providing an opening to an analytical combustion furnace having an input port for receiving a holder for an analytical sample for the combustion of the sample for the analysis of the byproducts of combustion. A purge block is coupled to the input port of the combustion furnace and has an input end for receiving the holder and a gas inlet and a gas outlet. A door selectively closes the input end of the purge block, and a pressurized seal is coupled between the purge block and the door. A source of purging gas is coupled to the gas inlet of the purge block for pressurizing the seal. The gas outlet of the purge block communicates with the seal to allow purging gas to escape the area of the seal in a controlled manner.

Further, the invention contemplates including a pressurized seal surrounding a push rod, which seal is pressurized by a purging gas to continuously purge the entry of the push rod into the purge block, thereby eliminating atmospheric contamination.

These and other features, objects and advantages of the present invention will become apparent upon reading the following description thereof together with reference to the accompanying drawings.

DETAILED DESCRIPTION OF THE PREFERRED EMBODIMENT

Figure 1:
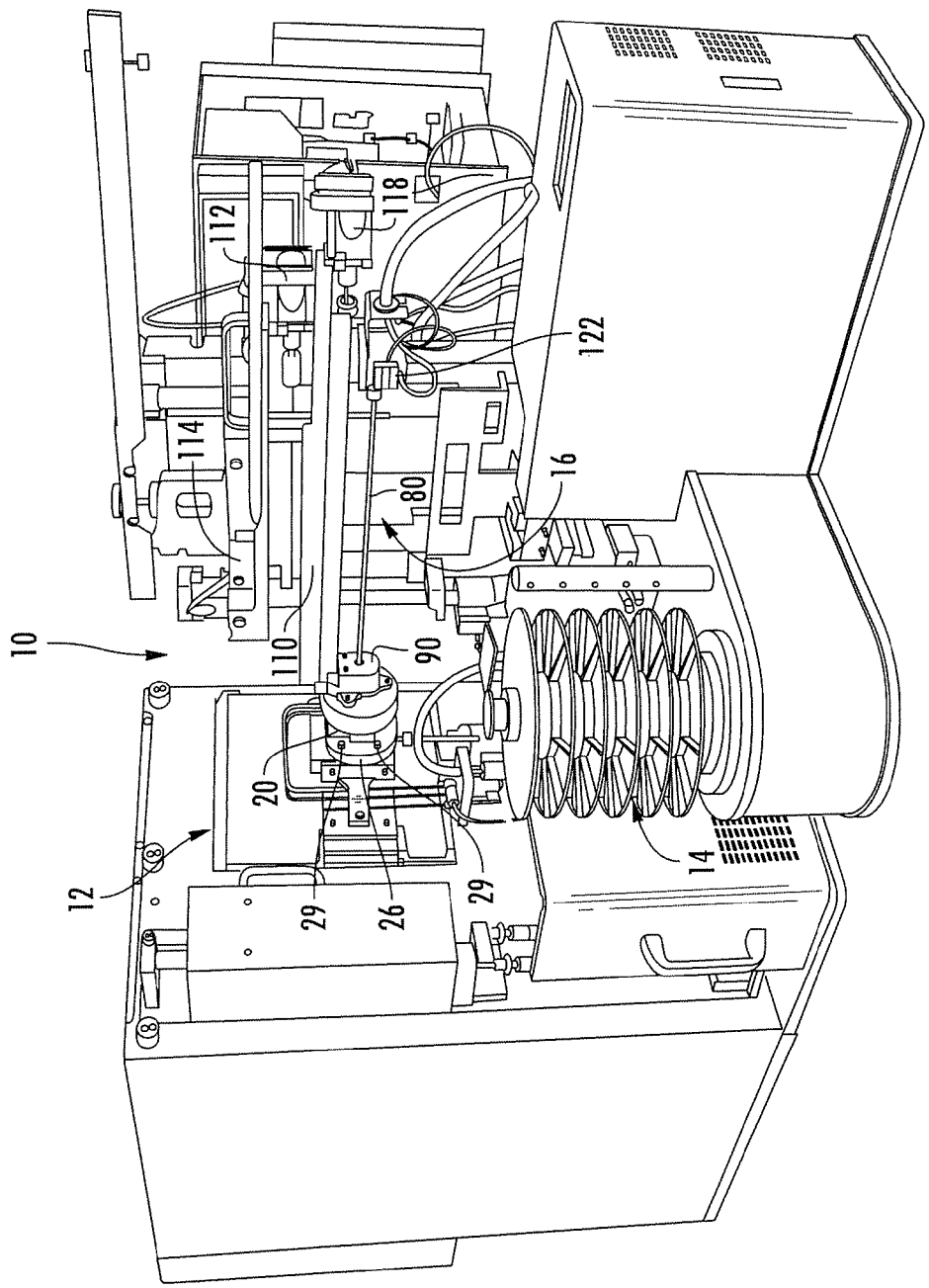
FIG. 1 is a perspective view of a combustion furnace utilizing the pressurized gas seals of the present invention.
Figure 2:
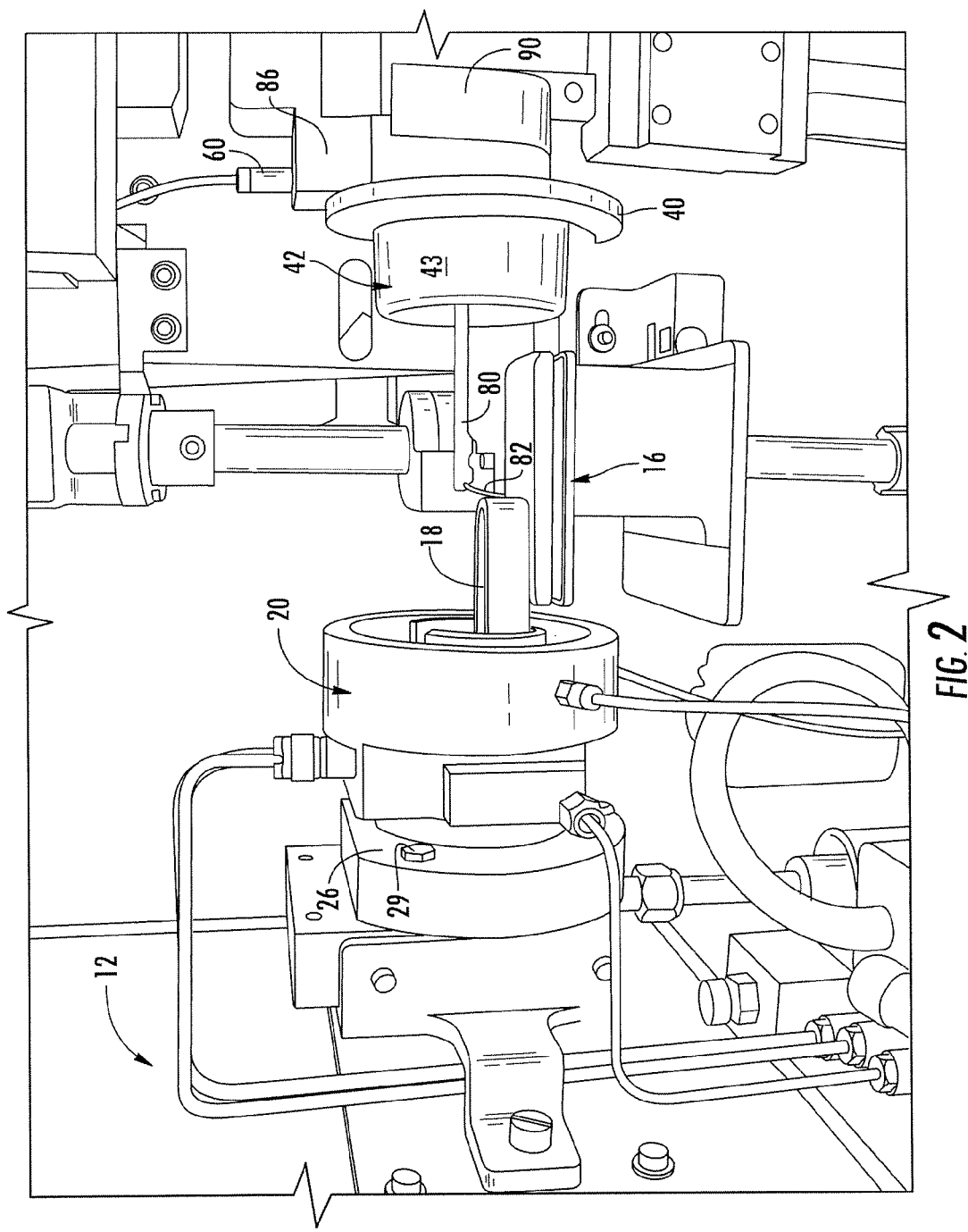
FIG. 2 is an enlarged perspective view of the input end of the purge block and its door in an open position and showing a combustion boat and push-pull rod for manipulating the combustion boat into the combustion furnace.
Figure 6:
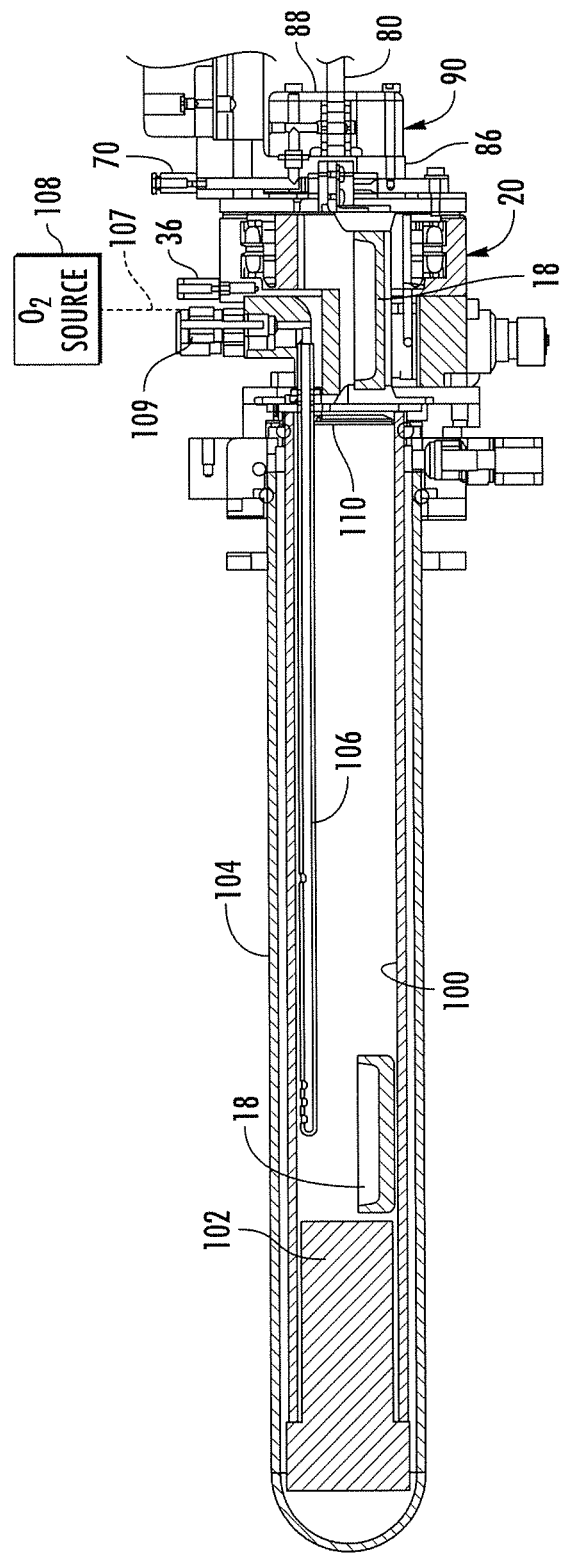
FIG. 6 is a fragmentary vertical cross-sectional view of the structure shown in FIG. 5.

Referring initially to FIG. 1, there is shown an analyzer 10 embodying the combustion furnace and pressurized gas purged seals of the present invention. Analyzer 10 can be a TruMAC® nitrogen analyzer, recently commercially available from the Assignee of the present invention, Leco Corporation of St. Joseph, Mich. Analyzer 10 includes several components including a furnace 12, a carousel 14 for holding ceramic combustion boats with specimens to be analyzed which are introduced by an elevator 16 into the inlet of purge block 20 of furnace 12, as illustrated in FIG. 2. The analyzer 10 is a nitrogen analyzer but, depending on the detection system employed, can analyze other elements, such as carbon, sulfur, and the like. Typically, with a nitrogen sample, a thermo-conductivity cell is employed in a detection system such as described in U.S. Pat. No. 5,233,308 issued Aug. 3, 1993, to Willis, the disclosure of which is incorporated herein by reference. Samples placed in a sample holder 18, such as a ceramic combustion boat (FIGS. 2, 6, and 10), will typically be solid 1 gram samples, although they can take other forms as well. The samples are introduced into the furnace 12 through a purge block 20 then into a combustion tube 100, as best seen in FIG. 6. The combustion system contained within furnace 12 can generally be of the type described in the above-identified U.S. Pat. No. 5,064,617.

Figure 5:
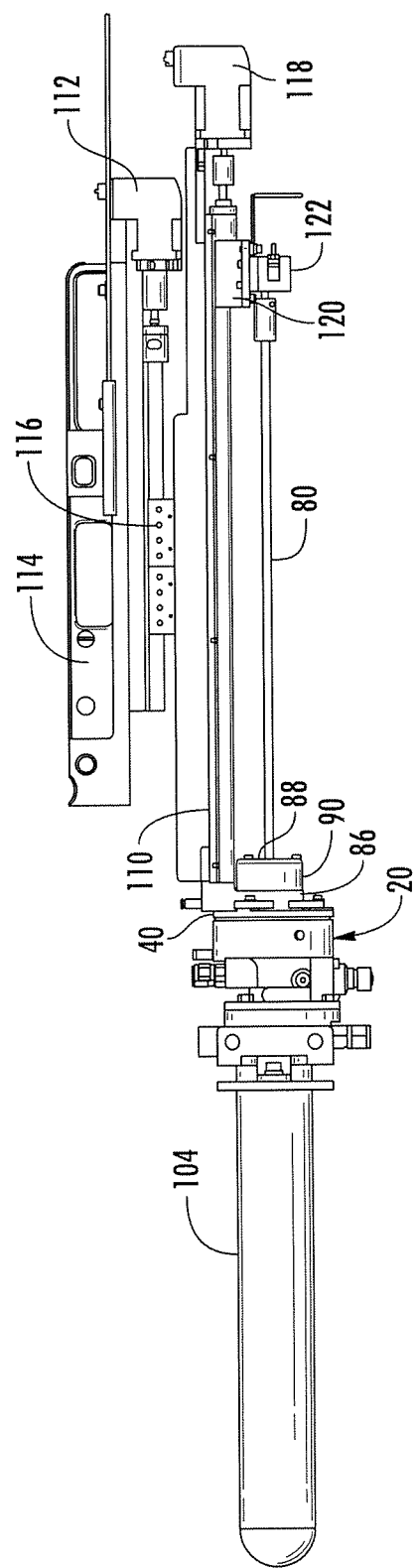
FIG. 5 is a left side elevational view of the combustion chamber, the purge block, and the push-pull rod assembly.
Figure 10:
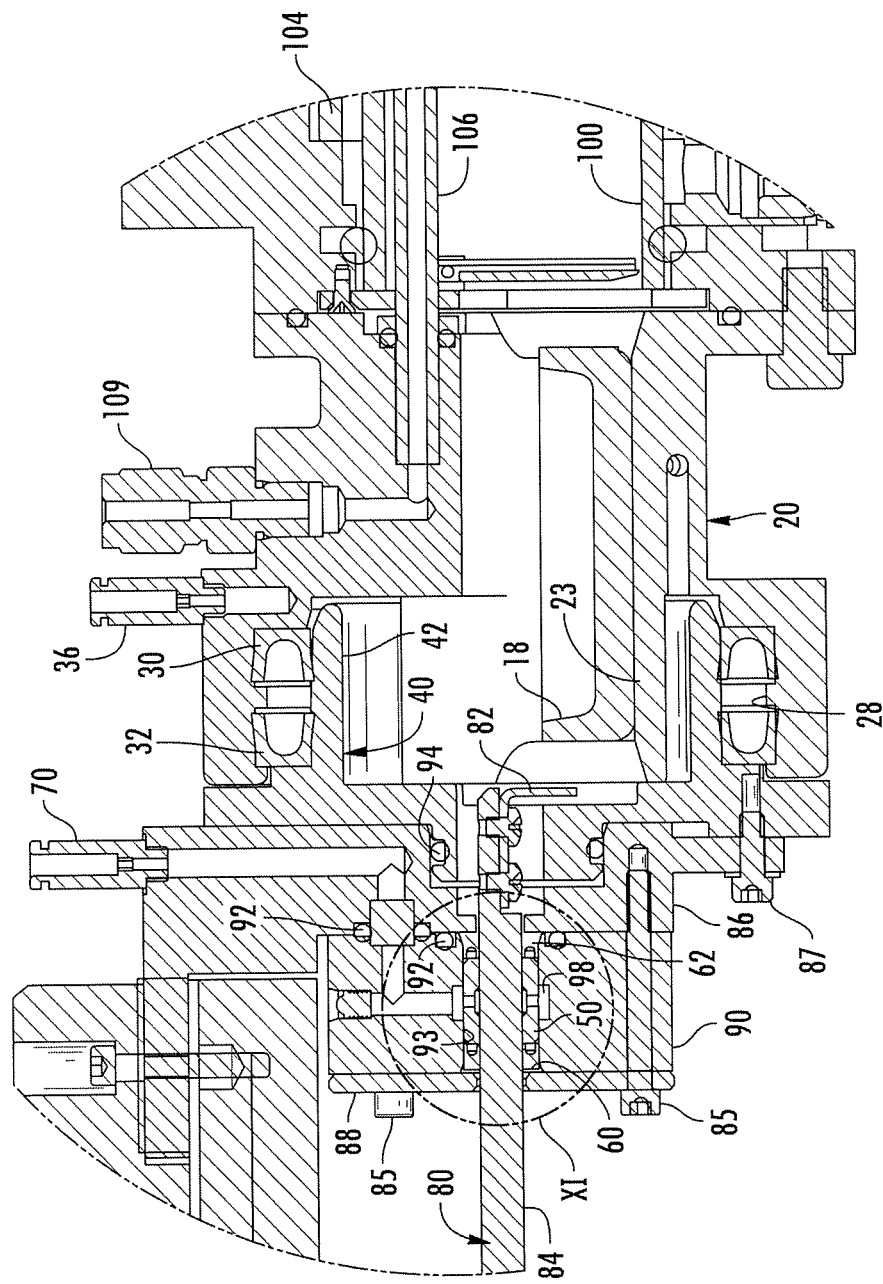
FIG. 10 is an enlarged fragmentary vertical cross-sectional view (reversed as viewed in FIG. 8) of the purge block and rod housing assembly.

The inner combustion tube 100 is a generally cylindrical tube (made of mullite) which positions a combustion boat 18 adjacent boat stop 102 and is enclosed within an outer closed-end cylindrical mullite combustion tube 104 (FIGS. 5 and 6). An oxygen lance 106 is supplied with a flow of oxygen from a source of purified oxygen 108, shown schematically in FIG. 6. Source 108 is UHP oxygen, which is 99.995% pure and is also coupled to the purge block gas inlet 34 (FIG. 7) and push-pull rod 80 housing 90 at oxygen inlet 70 (FIG. 10). Source 108 is coupled to the oxygen lance 106 through a fitting 109 (FIG. 6). The connection of the oxygen source 108 to the various fittings is shown schematically in FIG. 6 by the dashed line connectors 107, it being understood that the connections 107 are typically tubes with suitable gas-tight fittings, such as fitting 109 for transferring the flow of oxygen to the furnace components.

The purge block 20 is employed for admitting sample-holding combustion boats 18 into combustion tube 100 and withdrawing them subsequent to the combustion of a sample. Block 20 has an inlet end 22 leading to an internal annular cavity 24 for holding a sample-holding combustion boat prior to an analysis during a period of time sufficient for purging the atmospheric contamination from the combustion boat and sample once the door 40 for the purge block 20 is moved from an open position, seen in FIG. 4, to a closed position, shown in FIG. 3. Cavity 24 (FIG. 4) of purge block 20 includes a generally axially aligned, U-shaped support structure having a floor 23 for supporting a combustion boat 18, as seen in FIG. 6, once admitted to the inlet end 24 of the purge block. Purge block 20 is fixedly and sealably coupled to the input port 110 (FIG. 6) of the combustion system including combustion tube 100 by a generally circular flange 26, including O-ring seals 27 (FIG. 7) and suitable fasteners 29 which, as seen in FIGS. 1-4, sealably secure the outlet end of purge block 20 to the inlet 110 of furnace 12 and combustion tube 100. Thus, once assembled, purge block 20 is sealably secured to furnace 12 and the combustion tube components contained therein.

In order to admit specimens in holders, such as combustion boat 18, the door 40 of purge block 20 must be opened (FIGS. 2 and 4) and closed (FIGS. 1 and 3), and securely sealed against environmental contamination once closed and purged by the flow of oxygen from source 108. The push rod 80 is employed for pushing the combustion boat from elevator 16 into the furnace and moves with respect to the door 40 through a sealed housing 90 (FIGS. 8-11). Thus, there are two areas that must be positively sealed for maintaining a controlled environment during an analysis. First, the purge block holding the sample and combustion boat therein in the cavity 24 in the area between the door 40 and inlet end 22 of the purge block. Secondly, the interface between push rod 80 and housing 90 is sealed by pressurized seals which are constantly purged by the flow of purified oxygen from source 108 as described below.

The cup-shaped door 40 is coupled to housing 90 by a mounting plate 86 (FIGS. 8 and 10) to move in unison on a carriage 110 slideably mounted to the stationary frame 114 of analyzer 10 in a conventional manner using roller bearings and suitable guides. Carriage 110 is driven by a first motor 112 (FIGS. 1 and 3-5) also secured to stationary frame member 114 of the analyzer 10. This motor and a screw jack drive 116 extending between motor 112 and carriage 110 serve to move the door 40 and housing 90 between the open and closed positions seen in FIGS. 2 and 3, respectively. A second motor 118 (FIG. 5) and screw jack drive 120 are coupled to carriage 110 and are employed for advancing and retracting push-pull rod 80 with respect to housing 90 with motor 118 traveling with carriage 110 as the door 40 moves between open and closed positions. An actuator 122 is coupled to rod 80 and is employed for rotating the rod, such that an L-shaped pushing element 82 (FIGS. 2 and 10) at the end of the rod can be in a position as shown in FIG. 2 for engaging the trailing edge of combustion boat 18 for pushing the boat as rod 80 is advanced into the combustion tube 100. Subsequently, upon completion of combustion, actuator 122 rotates the rod 80 90°, such that rod 80 can be advanced to position element 82 on the leading edge of the boat 18. Actuator 122 then rotates rod 80 90° for engaging the leading edge of boat 18 withdrawing the boat from the combustion chamber in a manner described in U.S. Pat. No. 5,314,662 (noted above). Housing 90 and mounting plate 86 are sealably secured together by O-rings 92 (FIGS. 8 and 10) and fasteners 85 extending through outer cover plate 88 (FIGS. 3, 4, 8, and 10). The improved sealing mechanism for the internal cavity 24 of purge block 20 and the combustion tube 100 is now described in connection with FIGS. 4, 7, 8, and 10.

Figure 3:
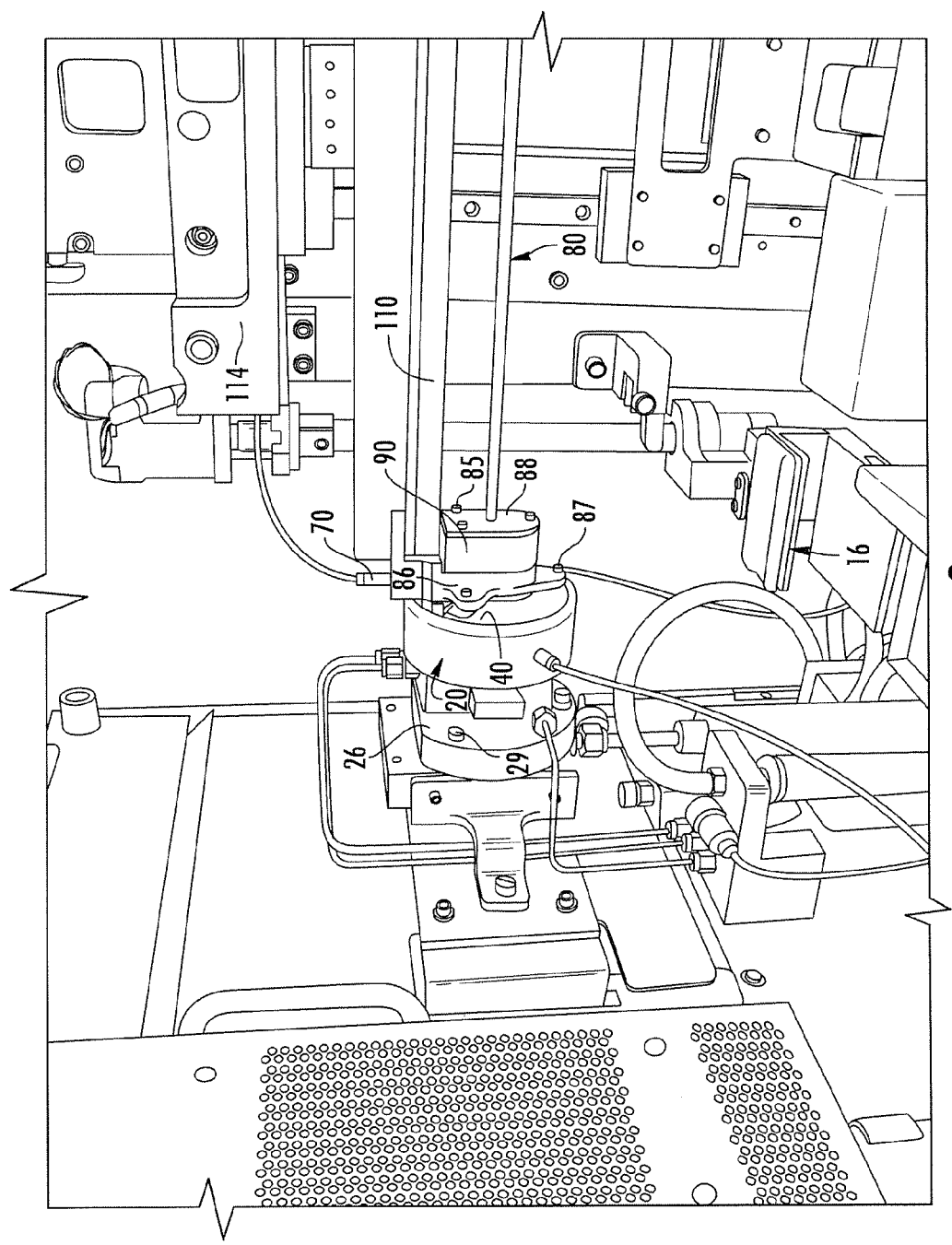
FIG. 3 is a perspective view of the purge block and push-pull rod assembly, shown in a closed position, for the combustion and analysis of a specimen.
Figure 4:
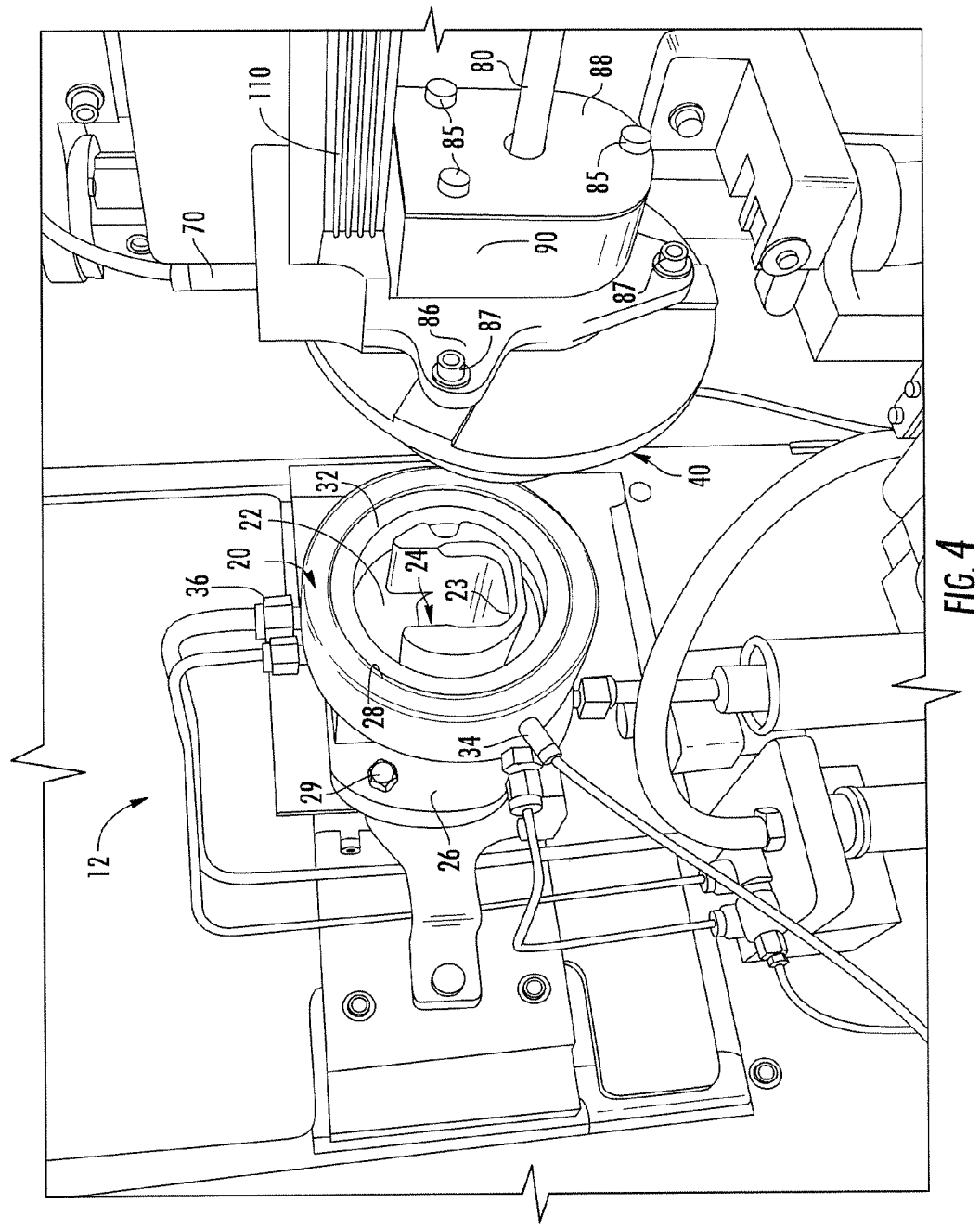
FIG. 4 is a perspective view of the furnace purge block and push-pull rod assembly shown in an open position.
Figure 7:
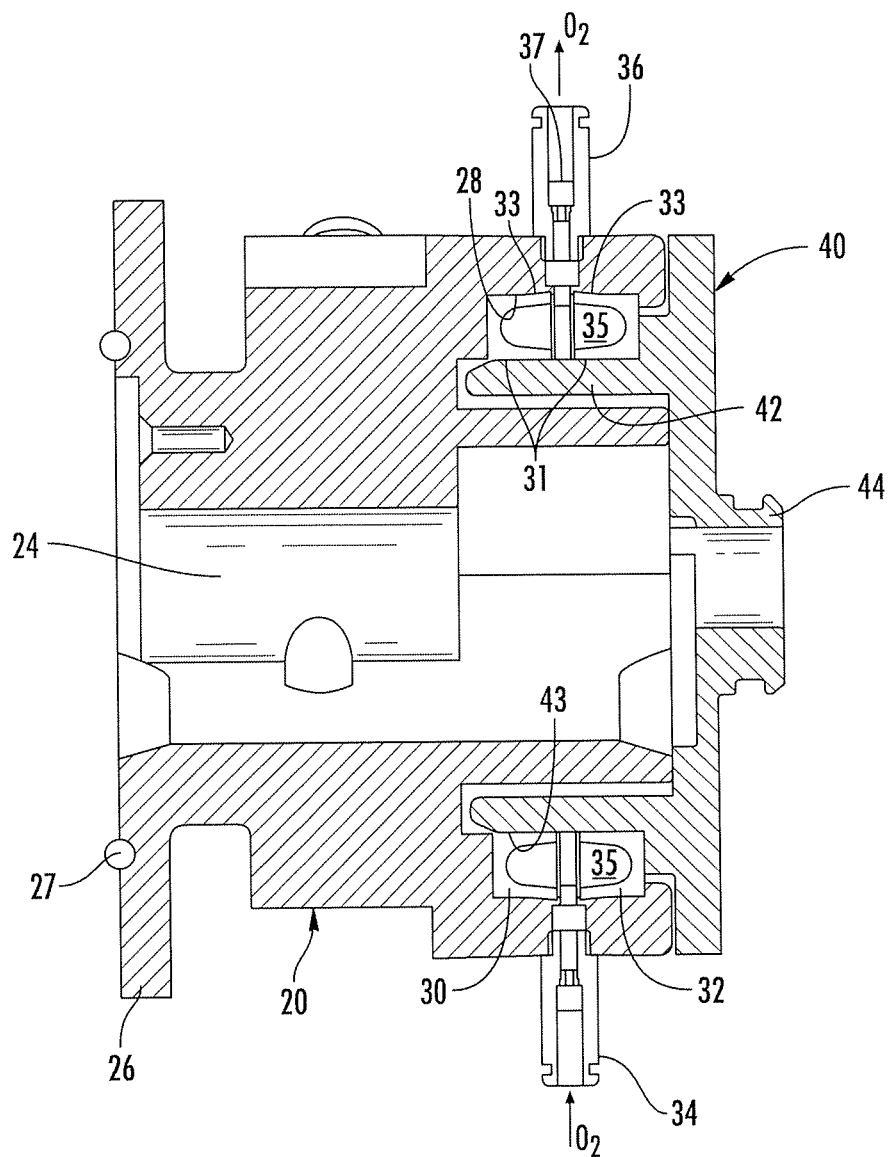
FIG. 7 is an enlarged vertical cross-sectional view of the purge block and door.
Figure 8:
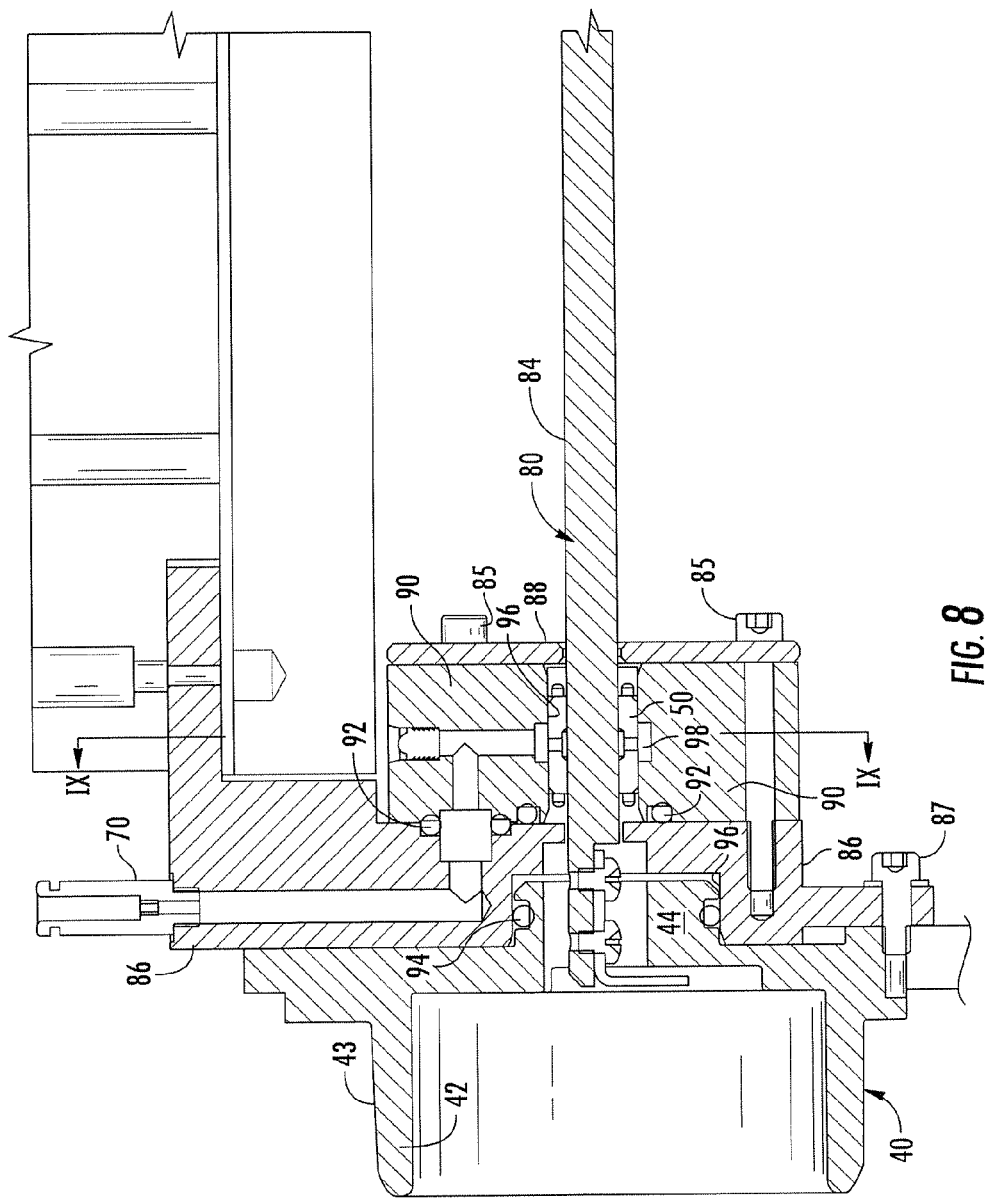
FIG. 8 is an enlarged cross-sectional view of the door for the purge block, the housing for the push-pull rod, and an interface plate.
Figure 9:
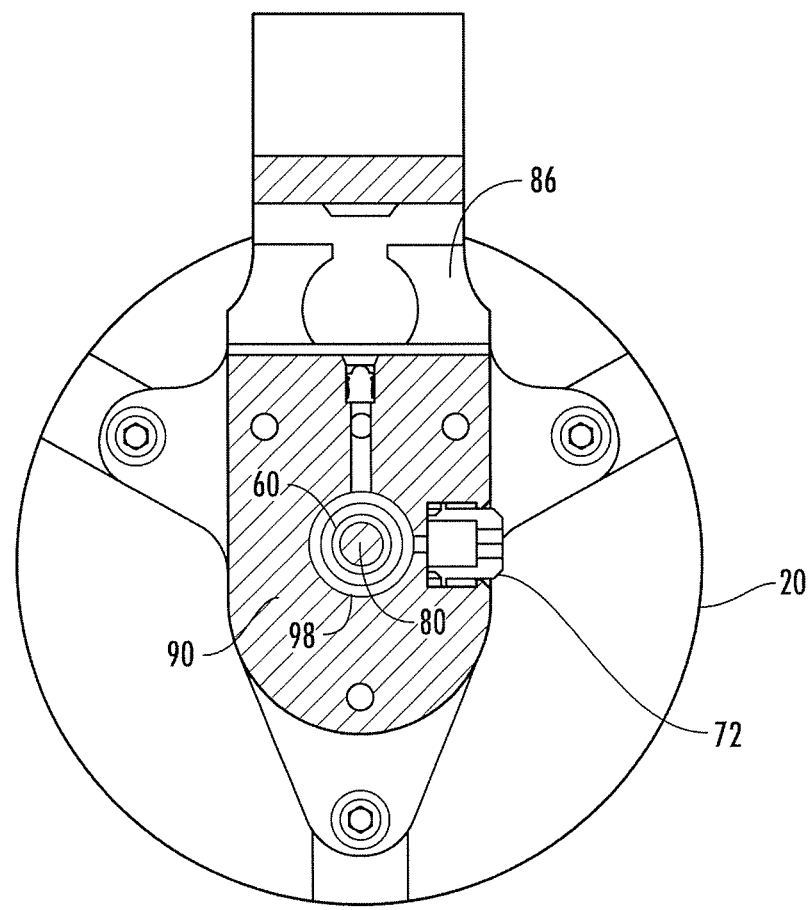
FIG. 9 is a cross-sectional view of the housing for the push-pull rod, taken along section line IX-IX in FIG. 8.

The inlet end 22 of purge block 20 is generally annular, as seen in FIG. 4, and includes an annular outer recess 28 (FIGS. 7 and 10) for receiving a pair of opposed facing spaced-apart annular cup-shaped seals 30 and 32 (FIG. 7). Seals 30, 32 are preferably made of nitrile/Viton® having a durometer hardness of about 60 or 70. They are sized to fit in close relationship with wall 28 of block 20 and surface 43 of door 40, as best seen in FIG. 7. Seals 30 and 32 are positioned in spaced relationship on opposite sides of an oxygen inlet 34 and an oxygen outlet 36, which includes a flow restrictor 37. Oxygen is supplied between seals 30 and 32 at a pressure of about 10 psi and a flow rate of approximately 100 cc/min to pressurize the seals 30, 32 and urge their inner and outer cylindrical surfaces 31, 33 tightly against the inner cylindrical wall 28 of block 20 and the outer surface 43 of the annular flange 42 of cup-shaped door 40. As best seen in FIGS. 2, 7 and 10, the annular flange 42 of door 40 extends within the annular space between wall 28 of block 20 and surrounds the floor 23 of the purge block. The outer surface 43 (FIGS. 2, 7 and 8) of annular flange 42 of door 40 engages surfaces 31 of seals 30 and 32. Upon actuation of motor 112 to position the door 40 in a closed position, as seen in FIGS. 1 and 3, purging gas from source 108 is supplied through inlet 34 into the annular volume 35 between cup seals 30 and 32 to pressurize the seals to provide a tight seal between door 40 and purge block 20. The continuous flow of oxygen through restricted outlet 36 initially for approximately two minutes together with oxygen through lance 106 is sufficient to purge the cavity 24 and combustion chamber 100, as well as pressurize seals 30 and 32 to a tightly sealed position. The oxygen continues to flow during the subsequent heating of the furnace and combustion of a sample, which typically takes from four to five minutes.

The pressurized volume 35 between seals 30 and 32 prevents the admission of atmospheric contaminants during the combustion of a specimen.

The concept of providing a pressurized flow of purging gas, such as oxygen, to both provide pressurized sealing to the purge block and purge contaminants is likewise applied to the interface between push-pull rod 80 and its housing 90. Housing mounting plate 86 is sealably secured to the door 40 through the O-rings 94 (FIG. 8) over an annular door coupling 44, as best seen in FIG. 7. Housing 90, in turn, is sealably coupled to plate 86 by O-rings 92 and fasteners 85. Housing mounting plate 86 includes an annular opening 96 (FIG. 8) which receives door coupling 44 to sealably couple housing 90 to door 40. Suitable fasteners, such as fasteners 87, secure plate 86 to door 40.

Figure 11:
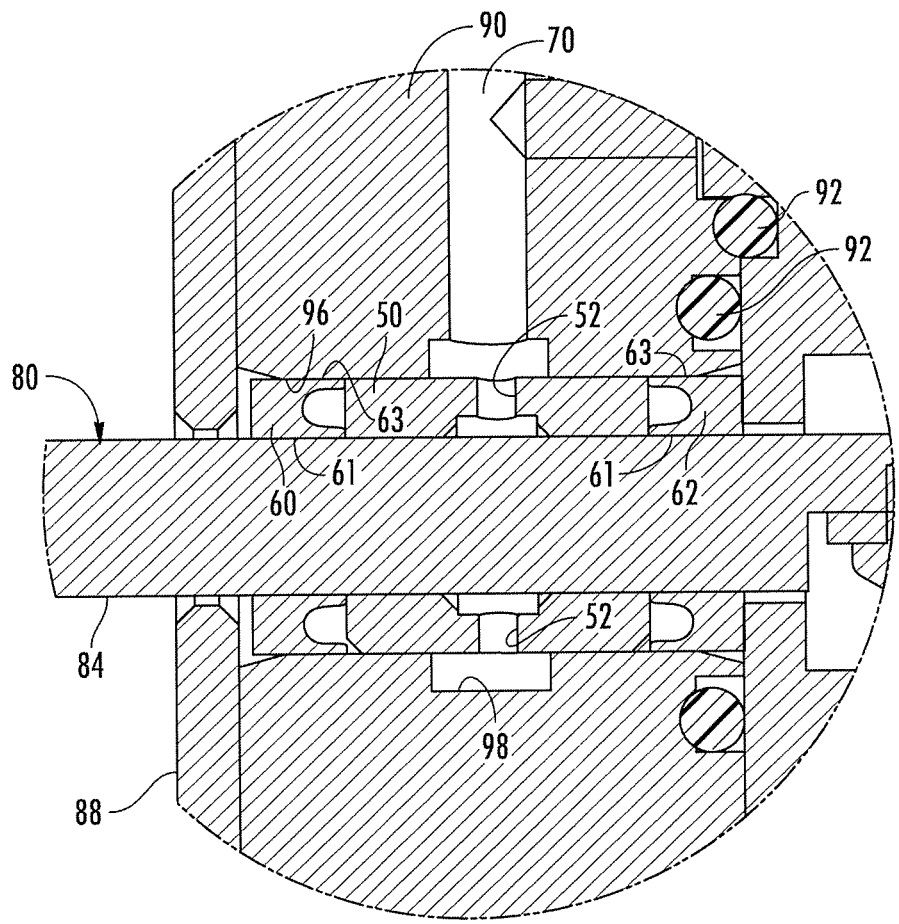
FIG. 11 is a greatly enlarged cross-sectional view of the circled area XI in FIG. 10.

As best seen in FIGS. 8-11, housing 90 includes an axially extending cylindrical port 93 which receives a ported bearing 50 for rotatably and axially supporting the motion of push rod 80 within housing 90. Ported bearing 50 can be made of a suitable bearing material, such as phosphorous bronze or the like, and includes radially extending ports 52 which communicate with an annular recess 98 (FIG. 11) formed in housing 90, such that oxygen from an oxygen inlet 70 (FIGS. 8, 10, and 11) coupled to source 108 can flow in the area surrounding rod 80 through the ported bearing 50. On opposite sides of ported bearing 50 are opposed facing cup seals 60 and 62. Seals 60, 62 are made of Turcite® (PTFE with carbon graphite) having a durometer hardness of about 70 and are sized to closely surround the outer surface 84 of rod 80 and engage port 96 of housing 90, as best seen in FIG. 11. Oxygen from supply 108 is admitted through oxygen inlet 70 and exits the ported area in annular recess 98 through restricted exhaust port 72 (FIG. 9) also communicating with the annular recess 98. The oxygen is supplied at inlet 70 at approximately 10 psi with a flow rate of 5 cc/min to pressurize the surfaces 61 of cup seals 60 and 62 against the outer cylindrical surface 84 of rod 80 and the outer surfaces 63 of seals 60, 62 against port 96. This assures a secure seal between rod 80 and housing 90 as the rod is moved axially and rotated during the admission of a sample-holding combustion boat 18 and its subsequent withdrawal by operation of the rod 80. The continuous supply of pressurized purging purified oxygen through recess 98 in the area between seals 60 and 62 purges any contaminants that may exist on rod 80 and also prevents admission of any atmospheric contamination in the area of the rod interface with housing 90. Housing 90 includes an outer cover plate 88 (FIGS. 8 and 10) and an interface mounting plate 86 between the housing 90 and door 40. Plate 86 is sealably secured to housing 90 by fasteners 85 and O-rings 92 and subsequently to door 40 by fasteners 87. In some embodiments, the housing may be of unitary construction and coupled directly to the door or part of the door itself.

Thus, in the two critical areas of sealing the combustion furnace associated with analyzer 10, namely, the purge block 20 and the housing 90 for push-pull rod 80, employ pressurized seals and continuous pressurized flow of purified oxygen to prevent the admission of contaminants from the atmosphere during the loading and unloading of a sample as well as purging of the purge block and rod areas before and during an analysis of a specimen. This allows extremely low levels of analytes to be measured without contamination from the surrounding environment. The analyzer itself can be of the type commercially available from Leco Corporation of St. Joseph, Mich.

It will become apparent to those skilled in the art that various modifications to the preferred embodiment of the invention as described herein can be made without departing from the spirit or scope of the invention as defined by the appended claims.

The invention claimed is:

1. A purge seal for an analytical furnace comprising:
 a combustion furnace having an input port for receiving a holder for an analytical sample for the combustion of the sample for the analysis of the byproducts of combustion;
 a purge block coupled to said input port of said combustion furnace, said purge block having an input end for receiving said holder and a gas inlet and a gas outlet, said input end of said purge block having an annular channel;
 a door for selectively closing said input end of said purge block, said door including an annular flange which extends within said annular channel of said purge block;
 a pair of axially spaced annular cup-shaped seals positioned in opposed facing relationship on opposite sides of said gas inlet and said gas outlet coupled within said annular channel of said purge block and extending radially between said purge block and said door;
 a source of purging gas coupled to said gas inlet of said purge block for pressurizing said seals; and
 said gas outlet of said purge block communicating with said seals to allow purging gas to escape the area of said seals.

2. The seal as defined in claim 1 wherein said purge block includes a floor for supporting said holder.

3. The seal as defined in claim 2 wherein said input end of said purge block includes an annular flange spaced from said floor and defining said annular channel therebetween, and wherein said annular flange of said door extends into said annular channel when said door is in a closed position with respect to said purge block.

4. The seal as defined in claim 1 wherein said annular flange of said purge block includes a radially outwardly extending recess for receiving said pressurized seal.

5. The seal as defined in claim 1 wherein said gas outlet includes a flow restrictor.

6. The seal as defined in claim 1 wherein said door further includes a central aperture for receiving a push-pull rod therein.

7. The seal as defined in claim 6 and further including a housing sealably coupled to said door and having a cylindrical port and seal for sealably supporting said push-pull rod therein.

8. The seal as defined in claim 7 wherein said seal includes a pair of axially spaced opposed cup-shaped seals.

9. The seal as defined in claim 8 wherein said housing includes a ported bearing in said cylindrical port for supporting said push-pull rod and a gas inlet coupled to said source of purging gas for receiving a purging gas to pressurize said cup-shaped seals through said ported bearing and a gas outlet.

10. The seal as defined in claim 9 wherein said gas outlet includes a flow restrictor.

11. The seal as defined in claim 10 wherein said source of purging gas is purified oxygen.

12. A purge seal for an analytical furnace comprising:
 a combustion furnace having an input port for receiving a holder for an analytical sample for the combustion of the sample for the analysis of the byproducts of combustion;
 a housing coupled to said input port of said furnace, said housing movably supporting a push-pull rod for pushing a sample holder into said furnace through said input port and for withdrawing said holder from said furnace, wherein said housing has an axial port extending radially outwardly for receiving a pair of opposed facing cup-shaped seals, a gas inlet and a gas outlet;

said seals coupled in said axial port and extending radially between said housing and said rod;

a source of purging gas coupled to said gas inlet of said housing for pressurizing said seals; and said gas outlet of said housing communicating with said seals to allow purging gas to escape the area of said seals.

13. The furnace as defined in claim 12 wherein said pressurized seals includes an annular cup-shaped seal.

14. The furnace as defined in claim 13 wherein said seal includes a pair of axially spaced annular cup-shaped seals positioned in opposed facing relationship on opposite sides of said gas inlet and said gas outlet.

15. The furnace as defined in claim 14 wherein said gas outlet includes a flow restrictor.

16. The furnace as defined in claim 12 wherein said housing includes a ported bearing extending between said rod and said housing and wherein said ported bearing is coupled to said source of purging gas.

17. An analyzer for analyzing the byproducts of combustion, said analyzer comprising:

a combustion furnace for heating a specimen held in a combustion holder to a temperature of from about 1000° C. to about 1500° C., said furnace including an input port;

a purge block coupled to said input port of said combustion furnace, said purge block having an input end for receiving said holder and a gas inlet and a gas outlet;

a door for selectively closing said input end of said purge block;

a pair of spaced-apart pressurized seals coupled between said purge block and said door;

a source of purging gas coupled to said gas inlet of said purge block for pressurizing said seals;

said gas outlet of said purge block communicating with said seals to allow purging gas to escape the area of said seals; and wherein said input end of said purge block includes one of an annular channel and flange and said door includes the other of an annular channel and flange, such that, when said door engages said purge block, said pressurized seals extend radially between said purge block and said door.

18. The analyzer as defined in claim 17 and further including:

a housing coupled to said input end of said purge block, said housing movably supporting a push-pull rod for pushing a sample holder into said furnace through said input port and for withdrawing said holder from said furnace, wherein said housing has a gas inlet and a gas outlet;

a second pair of spaced-apart pressurized seals coupled between said housing and said rod;

a source of purging gas coupled to said gas inlet of said housing for pressurizing said second seal; and said gas outlet of said housing communicating with said second pair of seals to allow purging gas to escape the area of said second pair of seals.

19. The analyzer as defined in claim 18 wherein said first and second pairs of pressurized seals include annular cup-shaped seals.

20. The analyzer as defined in claim 19 wherein said first and second pairs of seals include a pair of axially spaced annular cup-shaped seals positioned in opposed facing relationship on opposite sides of said respective gas inlets and said respective gas outlets.

21. The analyzer as defined in claim 20 wherein each of said gas outlets includes a flow restrictor.

22. The analyzer as defined in claim 21 wherein said housing includes a ported bearing extending between said rod and said housing and wherein said ported bearing is coupled to said source of purging gas.

* * * * *